(12) United States Patent
Parthasaradhi Reddy et al.

(10) Patent No.: US 8,481,554 B2
(45) Date of Patent: *Jul. 9, 2013

(54) SOLID ORAL DOSAGE FORMS OF LAMIVUDINE

(75) Inventors: Bandi Parthasaradhi Reddy, Hyderabad (IN); Male Srinivas Reddy, Hyderabad (IN); Pothireddy Venkateswar Reddy, Hyderabad (IN); Muppidi Vanaja Kumari, Hyderabad (IN)

(73) Assignee: Hetero Research Foundation (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/322,536

(22) PCT Filed: May 27, 2009

(86) PCT No.: PCT/IN2009/000305
§ 371 (c)(1),
(2), (4) Date: Nov. 25, 2011

(87) PCT Pub. No.: WO2010/137027
PCT Pub. Date: Dec. 2, 2010

(65) Prior Publication Data
US 2012/0077772 A1    Mar. 29, 2012

(51) Int. Cl.
*A61K 31/505*    (2006.01)
*C07D 411/04*    (2006.01)

(52) U.S. Cl.
USPC .......................................... 514/274; 544/317

(58) Field of Classification Search
USPC .......................................... 514/274; 544/317
See application file for complete search history.

(56) References Cited

U.S. PATENT DOCUMENTS

| | | | |
|---|---|---|---|
| 5,905,082 A * | 5/1999 | Roberts et al. | 514/274 |
| 6,113,920 A | 9/2000 | Maye et al. | |
| RE39,155 E | 7/2006 | Belleau et al. | |
| 2009/0098192 A1 | 4/2009 | Fuisz | |
| 2011/0137034 A1* | 6/2011 | Parthasaradhi Reddy et al. | 544/317 |

FOREIGN PATENT DOCUMENTS

| | | |
|---|---|---|
| EP | 1180033 A2 | 11/2000 |
| WO | WO 92/20344 A1 | 11/1992 |
| WO | WO 96/01110 A2 | 1/1996 |
| WO | WO 00/18383 A2 | 4/2000 |
| WO | WO 2004/069198 A2 | 8/2004 |
| WO | WO 2007/068934 A2 | 6/2007 |
| WO | WO 2007/119248 A1 | 10/2007 |
| WO | WO 2008/009689 A1 | 1/2008 |
| WO | WO 2009/086046 A1 | 7/2009 |
| WO | WO 2009/31026 A2 | 12/2009 |

* cited by examiner

*Primary Examiner* — James O Wilson
*Assistant Examiner* — Ebenezer O Sackey
(74) *Attorney, Agent, or Firm* — Cantor Colburn LLP

(57) ABSTRACT

The present invention relates to the oral solid pharmaceutical composition comprising lamivudine or a pharmaceutically acceptable salt thereof with isomalt as a filler. The present invention also relate to the combination of lamivudine and other Anti-HIV agents. Thus, for example, the present invention provides a stable tablet formulation comprising lamivudine, isomalt, crospovidone, calcium stearate and opadry white.

16 Claims, No Drawings

SOLID ORAL DOSAGE FORMS OF LAMIVUDINE

CROSS-REFERENCE TO RELATED APPLICATIONS

This application is a 371 of PCT/IN2009/000305 filed May 27, 2009, under provisions of the International Convention for the protection of Industrial Property, which are incorporated herein by reference.

FIELD OF THE INVENTION

The present invention relates to the oral solid pharmaceutical composition comprising lamivudine or a pharmaceutically acceptable salt thereof with isomalt as a filler. The present invention also relate to the combination of lamivudine and other Anti-HIV agents.

BACKGROUND OF THE INVENTION

Lamivudine, chemically, (2R-cis)-4-Amino-1-[2-(hydroxymethyl)-1,3-oxathiolan-5-yl]-2(IH)-pyrimidinone; (−)-2'-deoxy-3'-thiacytidine; (−)-1-[(2R,5S)-2-(hydroxymethyl)-1,3-oxathiolan-5-yl]cystosine; or 3TC is a reverse transcriptase inhibitor. The therapeutic uses of lamivudine and related compounds and their preparations were disclosed in WO 91/17159.

Lamivudine is also useful in the treatment of hepatitis B infection as disclosed in U.S. RE39155. WO Patent Publication No. 92/20344 disclosed a method of treatment of HIV infection and other viral infection with lamivudine in combination with other antiviral agents such as Zidovudine, chemically 3'-azido-3'-deoxythymidine.

Lamivudine is commercially available as 100 mg, 150 mg and 300 mg tablets; 10 mg/ml in 240 ml oral solution. It is sold under the name EPIVIR.

U.S. Pat. No. 5,905,082 reported that the needle shaped crystals of form I are not favored for pharmaceutical formulation into solid dosage forms because of poor flow characteristics.

WO Patent Application Publication No. 2009/031026 described a novel pharmaceutical composition of lamivudine and cyclodextrin complex.

EP Patent No. 1,180,033 disclosed lamivudine, lactose, starch, crystalline cellulose, hydroxypropyl cellulose and talc in pharmaceutical formulation.

The combination composition of lamivudine and zidovudine is commercially available as 150 mg and 300 mg tablets. It is sold under the name COMBIVIR.

U.S. Pat. No. 6,113,920 disclosed a pharmaceutical composition comprising two active pharmaceutical ingredients namely lamivudine and zidovudine and a pharmaceutically acceptable glidant ingredient in the form of a film coated tablet.

WO Patent Application Publication No. 00/18383 described antiviral combination of (S)-2-ethyl-7-fluoro-3-oxo-3,4-dihydro-2H-quinoxaline-1-carboxylic acid isopropyl ester and zidovudine and/or lamivudine.

WO Patent Application Publication No. 96/01110 described a combination of zidovudine, lamivudine and loviride for the treatment of HIV infections and AIDS.

WO Patent Application Publication No. 2007/068934 described combination of lamivudine with tenfovir disoproxil fumarate.

Lamivudine exhibits polymorphism. Form I and Form II are reported in U.S. Pat. No. 5,905,082, Form III are disclosed in WO 2007/119248.

All the above mentioned patents are incorporated by references.

In spite of all the above disclosed formulations of lamivudine, still there is a need for pharmaceutical formulations that have good flow properties, good compressibility and stability in terms of polymorphic form during and after formulation.

Thus an object of the present invention is to provide a pharmaceutical formulation containing lamivudine, having good flow properties, good compressibility and bulk density, all of which enable a formulation that can be produced without any difficulty.

Another object of the present invention is to provide the oral tablet formulation of lamivudine with isomalt as filler, the oral solid pharmaceutical formulation being capable of avoiding capping of lamivudine with any polymorphic forms.

Another object of the present invention provides a process for preparing of lamivudine and/or in combination with other anti-Human immunodeficiency virus (anti-HIV) agents.

Another object of the present invention is to provide a pharmaceutical formulation of lamivudine in combination with other anti-HIV agents, having good flow properties, good compressibility and bulk density, which enable a formulation that can be produced without any difficulty.

Another object of the present invention is to provide suitable pharmaceutical formulation of lamivudine and/or in combination with other anti-HIV agents.

Yet, another object of the present invention is to provide stable oral dosage forms of lamivudine.

DETAILED DESCRIPTION OF THE INVENTION

According to one aspect of the present invention, there is provided the oral solid pharmaceutical composition comprising lamivudine or a pharmaceutically acceptable salts thereof with isomalt as a filler and optionally one or more additional excipients.

Isomalt is a sugar substitute, a disaccharide composed of two sugars glucose and mannitol that are useful as pharmaceuticaly acceptable excipients. It is an odourless, crystalline substance containing about 5% water of crystallization.

The pharmaceutical composition of the present invention has been found to have good flow property, good compressibility and bulk density in comparison with literature oral solid dosage forms.

Surprisingly, it has been found that the pharmaceutical compositions of the present invention not only display the enhanced flow characteristics and dissolution, but also display the improved characteristics associated with polymorphic forms, which does not undergo any change in crystal structure.

Capping is the term used, when the upper or lower segment of the tablet separates horizontally, either partially or completely from the main body of a tablet and comes off as a cap, during ejection from the tablet press.

The tablet formulation of present invention is also capable of avoiding capping of lamivudine with any polymorphic forms.

A pharmaceutical composition of the present invention may also comprise one or more other excipients such as a filler agent, a disintegrant agent, a binder, a glidant and a lubricant, preferably oral solid dosage forms.

The pharmaceutical composition may be for example, in the form of a tablet, a caplet, pellets, a capsule, granules, a pill, powder or a sachet.

Preferably, the pharmaceutical composition is in the form of a tablet and a capsule. The capsule may contain powder, compressed powder or granules.

Still more preferably, the pharmaceutical composition is in the form of a tablet.

Preferably, lamivudine used in the oral solid pharmaceutical composition is in polymorphic form I, or form II, more preferably polymorphic form I.

In one embodiment of the present invention, the concentration of lamivudine to isomalt in the pharmaceutical composition is about 1:0.2 to about 1:4.

More preferably, the concentration of lamivudine to isomalt in the pharmaceutical composition is about 1:0.5 to about 1:2.

In another embodiment, the pharmaceutical composition of the present invention comprises a filler agent, a disintegrant agent, and a lubricant, wherein said solid pharmaceutical composition comprising lamivudine is in polymorphic form I.

Excipient selection depends on various factors, such as, the choice of active ingredient percentage, the objectives of the tablet formulation development and method of manufacture. The foremost property an excipient must possess is compatibility with active ingredients.

Preferably, the pharmaceutically acceptable excipients in accordance with the invention include at least one filler agent (in addition to isomalt) and/or at least one disintegrant agent, and/or at least one lubricant.

Preferably, the filler includes calcium carbonate, dibasic calcium phosphate, lactose, magnesium carbonate, magnesium oxide, lactose anhydrous, microcrystalline cellulose, mannitol or mixtures thereof and more preferably isomalt and/or microcrystalline cellulose.

Preferably, the lubricants includes stearic acid, a salt of stearic acid, talc, sodium stearyl fumarate, calcium stearate, glyceryl behenate, magnesium silicate, magnesium trisilicate, hydrogenated castor oil or mixtures thereof and more preferably calcium stearate.

Preferably, the disintegrators includes sodium starch glycolate, starch, croscarmellose sodium, crospovidone, carboxymethyl cellulose calcium, carboxymethylcellulose sodium, magnesium aluminium silicate or mixtures thereof and more preferably crospovidone.

Preferably, the glidant includes colloidal anhydrous silica, talc or mixtures thereof.

Preferably, the binders includes hydroxypropyl cellulose, polyvinylpyrrolidone k-30, hydroxypropyl cellulose (low-substituted), starch or mixtures thereof and more preferably hydroxypropyl cellulose (low-substituted).

Other ingredients such as stabilizers and antiadherants, conventionally used for pharmaceutical formulations may also be included in the present formulation.

In according to another aspect of the present invention, there is provided the process for preparing the oral solid pharmaceutical composition which comprises mixing lamivudine or pharmaceutical acceptable salts thereof, isomalt and optionally one or more additional excipients.

It has been found that the pharmaceutical process of the present invention are physically stable to pharmaceutical unit operations such as compression, thereby making oral solid dosage of the present invention amenable to pharmaceutical compounding operations, such as for example, tabletting.

In preferred embodiment, lamivudine is mixed with one or more of the other excipients such as filler (in addition to isomalt), disintegrant agent, a binder, a glident or a lubricant.

Preferably, the oral solid pharmaceutical compositions are in the form of a tablet, a caplet, pellets, a capsule, granules, a pill, powder or a sachet and more preferably a tablet.

Preferably, the tablet compositions are prepared by process of direct compression, wet granulation or slugging, more preferably direct compression.

The tablet may also be optionally coated with a coating agent.

Preferably, lamivudine used in the process for preparing the oral solid pharmaceutical composition is in polymorphic form I, or form II, more preferably polymorphic form I.

A preferred embodiment of the invention suitable for forming tablet comprises in parts by weight from about 25% to about 80% lamivudine, from about 15% to about 80% isomalt and/or microcrystalline cellulose or lactose, from about 1% to about 10% crospovidone and/or croscarmellose sodium, from about 1% to about 10% povidone and/or hydroxypropyl cellulose, from about 0.125% to about 5% calcium stearate or magnesium stearate, from about 1% to about 4% opadry white. Optionally additional excipient/s may be used. The additional excipients include pharmaceutical lubricants, disintegrators, binders, glidants, fillers or mixtures thereof.

In according to another aspect of the present invention, there is provided the oral solid pharmaceutical composition comprising lamivudine or a pharmaceutically acceptable salt thereof with isomalt as a filler and in combination with other anti-HIV agents, optionally one or more additional excipients.

Preferably, the other Anti-HIV agents are zidovudine, abacavir, tenofovir disoproxil fumarate or a pharmaceutically acceptable salt thereof.

Preferably, lamivudine used in the oral solid pharmaceutical composition is in polymorphic form I, or form II, more preferably polymorphic form I.

A preferred embodiment of the present invention provides stable pharmaceutical formulations of combination of i) lamivudine and zidovudine; ii) lamivudine and abacavir; or iii) lamivudine and tenofovir disoproxil fumarate.

It has been found that the pharmaceutical composition of the present invention not only display the enhanced flow characteristics and dissolution, but also display the improved characteristics associated even with polymorphic forms, which does not undergo any change in crystal structure.

A pharmaceutical composition of the present invention may also comprise one or more other excipients such as a filler agent, a disintegrant agent, a binder, a glidant and a lubricant, preferably oral solid dosage forms.

The pharmaceutical composition may be for example, in the form of a tablet, a caplet, pellets, a capsule, granules, a pill, powder or a sachet.

Preferably, the pharmaceutical composition is in the form of a tablet and a capsule. The capsule may contain powder, compressed powder or granules.

Still more preferably, the pharmaceutical composition is in the form of a tablet.

Preferably, lamivudine used in the oral solid pharmaceutical composition is in polymorphic form I, or form II, more preferably polymorphic form I.

In another embodiment, the pharmaceutical composition of the present invention comprises a filler agent, a disintegrant agent, and a lubricant, wherein said solid pharmaceutical composition comprising lamivudine is in a polymorphic form I.

Excipient selection depends on various factors, such as, the choice of active ingredient percentage, the objectives of the tablet formulation development and method of manufacture. The foremost property an excipient must possess is compatibility with active ingredients.

Preferably, the pharmaceutically acceptable excipients in accordance with the invention include at least one filler agent (in addition to isomalt) and/or at least one disintegrant agent, and/or at least one lubricant.

Preferably, the filler includes calcium carbonate, dibasic calcium phosphate, lactose, magnesium carbonate, magnesium oxide, lactose anhydrous, microcrystalline cellulose, mannitol or mixtures thereof and more preferably isomalt and/or microcrystalline cellulose.

Preferably, the lubricants includes stearic acid, a salt of stearic acid, talc, sodium stearyl fumarate, calcium stearate, glyceryl behenate, magnesium silicate, magnesium trisilicate, hydrogenated castor oil or mixtures thereof and more preferably calcium stearate.

Preferably, the disintegrators includes sodium starch glycolate, starch, croscarmellose sodium, crospovidone, carboxymethyl cellulose calcium, carboxymethylcellulose sodium, magnesium aluminium silicate or mixtures thereof and more preferably crospovidone.

Preferably, the glidant includes colloidal anhydrous silica, talc or mixtures thereof.

Preferably, the binders includes hydroxypropyl cellulose, polyvinylpyrrolidone k-30, hydroxypropyl cellulose (low-substituted), starch or mixtures thereof and more preferably hydroxypropyl cellulose (low-substituted).

Other ingredients such as stabilizers and antiadherants, conventionally used for pharmaceutical formulations may also be included in the present formulation.

In according to another aspect of the present invention, there is provided the process for preparing the oral solid pharmaceutical composition, which comprises mixing lamivudine or pharmaceutically acceptable salts thereof with isomalt as filler and in combination with other Anti-HIV agents, and optionally one or more additional excipients.

Preferably, the other Anti-HIV agents are zidovudine, abacavir, tenfovir disoproxil fumarate or a pharmaceutically acceptable salt thereof.

It has been found that the pharmaceutical process of the present invention are physically stable to pharmaceutical unit operations such as compression, thereby making oral solid dosage of the present invention amenable to pharmaceutical compounding operations, such as for example, tabletting.

In preferred embodiment, lamivudine is mixed with one or more of the other excipients such as filler (in addition to isomalt), disintegrant agent, a binder, a glident or a lubricant.

Preferably, the oral solid pharmaceutical compositions are in the form of a tablet, a caplet, pellets, a capsule, granules, a pill, powder or a sachet and more preferably a tablet.

Preferably, the tablet compositions are prepared by process of direct compression, wet granulation or slugging, more preferably direct compression.

The tablet may also be optionally coated with a coating agent.

Preferably, lamivudine used in the process for preparing the oral solid pharmaceutical composition is in polymorphic form I, or form II, more preferably polymorphic form I.

A preferred embodiment of the invention suitable for forming lamivudine and zidovudine tablet comprises in parts by weight from about 10% to about 80% lamivudine, from about 15% to about 50% zidovudine, from about 15% to about 80% isomalt, from about 1% to about 10% crospovidone, from about 0.125% to about 2.5% calcium stearate and from about 1.5% to about 2.5% opadry white. Optionally additional excipient/s may be used. The additional excipients include pharmaceutical lubricants, disintegrators, binders, glidant, fillers or mixtures thereof.

A preferred embodiment of the invention suitable for forming lamivudine and tenfovir disoproxil fumarate tablet comprises in parts by weight from about 15% to about 75% lamivudine, from about 15% to about 60% tenfovir disoproxil fumarate, from about 20% to about 80% isomalt, from about 1% to about 10% crospovidone, from about 0.125% to about 2.5% calcium stearate and from about 1.5% to about 2.5% opadry white. Optionally additional excipient/s may be used. The additional excipients include pharmaceutical lubricants, disintegrators, binders, glidant, fillers or mixtures thereof.

A preferred embodiment of the invention suitable for forming lamivudine and abacavir tablet comprises in parts by weight from about 15% to about 70% lamivudine, from about 30% to about 75% abacavir sulfate, from about 1% to about 50% isomalt, from about 1% to about 10% low-substituted hydroxypropyl cellulose, from about 1% to about 10% croscarmellose sodium, from about 3% to about 25% microcrystalline cellulose, from about 1% to about 7% povidone K-29/32, from about 0.125% to about 2.5% colloidal silicon dioxide, from about 0.125% to about 2.5% magnesium stearate and from about 1.5% to about 2.5% opadry white. Optionally additional excipient/s may be used. The additional excipients include pharmaceutical lubricants, disintegrators, binders, glidents, fillers or mixtures thereof.

The pharmaceutical composition may be used for the treatment of Human immunodeficiency virus (HIV) and/or hepatitis B infection.

The following examples illustrate the present invention without, however, limiting the same thereof.

EXAMPLES

Example 1

Preparation of a Lamivudine Tablet wherein the Lamivudine is Present in the Form of Lamivudine with Isomalt This example demonstrates a tablet composition comprising lamivudine as an active pharmaceutical ingredient and one or more pharmaceutically acceptable excipients, wherein said lamivudine is present in the form of the lamivudine with isomalt, in accordance with an embodiment of the invention. This example further demonstrates a process for preparing a solid pharmaceutical composition in accordance with an embodiment of the invention.

The tablets were prepared using the materials listed in table.

| Component | Weight (mg)/Tablet | | | % (w/w) |
|---|---|---|---|---|
| Lamivudine (form I) | 100 | 150 | 300 | 50 |
| Isomalt | 82.7 | 124 | 248 | 41.33 |
| Crospovidone | 13.3 | 20 | 40 | 6.67 |
| Calcium Stearate | 4 | 6 | 12 | 2 |
| Tablet weight | 200 | 300 | 600 | — |
| Opadry White | 4 | 6 | 12 | 2 |

The tablets were manufactured using the procedure comprising the following steps: lamivudine, isomalt, crospovidone and calcium stearate were weighed, transferred into a blender, and mixed to form a homogeneous power mixture;

the resultant mixture was compressed into tablets of appropriate weight and hardness to obtain a lamivudine tablet; and optionally, the tablets can be coated.

Lamivudine tablets blend has better flow property and bulk density, which are important parameters for formulation listed below.

| Property | Form I | Form II |
|---|---|---|
| Bulk density (gm/cc) | 0.45 | 0.31 |
| Tap density (gm/cc) | 0.63 | 0.57 |
| Flow property (Angle of Repose) | 32 | 35 |

The results of dissolution studies of lamivudine tablets 300 mg and 100 mg are shown below

| Time (minutes) | Epivir 300 mg | Epivir-HBV 100 mg | Lamivudine polymorphic form I tablets 300 mg | Lamivudine polymorphic form I tablets 100 mg |
|---|---|---|---|---|
| 5 | 98 | 84 | 94 | 94 |
| 10 | 99 | 89 | 98 | 97 |
| 15 | 99 | 92 | 99 | 97 |
| 30 | 100 | 93 | 99 | 97 |
| 45 | 100 | 95 | 99 | 97 |

The example demonstrates the dissolution properties of the tablet prepared in accordance with the invention.

The tablets of the example 1 and commercially available lamivudine tablets (i.e., Epivir® 300 mg) were tested for in vitro drug release in 900 ml of 0.1N HCl using a USP-2 apparatus operating at a speed of 75 rpm and lamivudine tablets (i.e., Epivir®-HBV 100 mg) were tested for in vitro drug release in 900 ml of water using a USP-2 apparatus operating at a speed of 50 rpm. In both cases the values for the tablets of example 1 and the values for commercially available lamivudine tablets (i.e., Epivir® 300 mg and 100 mg) were greater than 85% in 15 minutes.

Lamivudine Tablets (Example 1) Stability Studies:

Stability studies were carried out at 40 deg C./75% RH and 60 deg C. for two months and were found that polymorphic form I did not undergo any transformation into other polymorphs of lamivudine.

Example 2

Example 1 was repeated using isomalt in different ratio.

| Component | Weight (mg)/Tablet | | | % (w/w) |
|---|---|---|---|---|
| Lamivudine (form I) | 100 | 150 | 300 | 75 |
| Isomalt | 22 | 33 | 66 | 16.5 |
| Crospovidone | 9.3 | 14 | 28 | 7 |
| Calcium Stearate | 2 | 3 | 6 | 1.5 |
| Tablet weight | 133.3 | 200 | 400 | — |
| Opadry White | 2.7 | 4 | 8 | 2 |

Example 3

Example 1 was repeated using isomalt in different ratio.

| Component | Weight (mg)/Tablet | | | % (w/w) |
|---|---|---|---|---|
| Lamivudine (form I) | 100 | 150 | 300 | 33.3 |
| Isomalt | 185 | 277.5 | 555 | 61.7 |
| Crospovidone | 12 | 18 | 36 | 4 |
| Calcium Stearate | 3 | 4.5 | 9 | 1 |
| Tablet weight | 300 | 450 | 900 | — |
| Opadry White | 6 | 9 | 18 | 2 |

The results of dissolution studies of lamivudine tablets 300 mg are shown below

| Time (minutes) | Epivir 300 mg | Lamivudine polymorphic form I tablets 300 mg |
|---|---|---|
| 5 | 98 | 94 |
| 10 | 99 | 97 |
| 20 | 99 | 97 |
| 30 | 100 | 97 |
| 45 | 100 | 98 |

Example 4

Lamivudine Tablets 100 Mg, 150 Mg and 300 Mg

| Component | Weight (mg)/Tablet | | | % (w/w) |
|---|---|---|---|---|
| Lamivudine (form I) | 100 | 150 | 300 | 50 |
| Isomalt | 30 | 45 | 90 | 15 |
| Microcrystalline cellulose | 44.67 | 67 | 134 | 22.33 |
| Croscarmellose sodium | 10 | 15 | 30 | 5 |
| Low-substituted hydroxy propyl cellulose | 7.33 | 11 | 22 | 3.67 |
| Povidone K-29/32 | 2.33 | 3.5 | 7 | 1.17 |
| Colloidal silicon dioxide | 1 | 1.5 | 3 | 0.5 |
| Magnesium stearate | 4.67 | 7 | 14 | 2.33 |
| Tablet weight | 200 | 300 | 600 | — |
| Opadry White | 4 | 6 | 12 | 2 |

The tablets were manufactured using the procedure comprising the following steps: lamivudine, isomalt, microcrystalline cellulose, croscarmellose sodium, low-substituted hydroxy propyl cellulose, povidone K-29/32, colloidal silicon dioxide and magnesium stearate were weighted, transferred into a blender, and mixed to form a homogeneous power mixture; the resultant mixture was compressed into tablets of appropriate weight and hardness to obtain a lamivudine tablet; and optionally, the tablets can be coated.

The results of dissolution studies of lamivudine tablets 300 mg are shown below

| Time (minutes) | Epivir 300 mg | Lamivudine polymorphic form I tablets 300 mg |
|---|---|---|
| 5 | 98 | 98 |
| 10 | 99 | 100 |
| 15 | 99 | 100 |
| 30 | 100 | 100 |
| 45 | 100 | 100 |

Example 5

Lamivudine Tablets 100 Mg, 150 Mg and 300 Mg

| Component | Weight (mg)/Tablet | | | % (w/w) |
|---|---|---|---|---|
| Lamivudine (form I) | 100 | 150 | 300 | 52.63 |
| Isomalt | 28.5 | 42.75 | 85.5 | 15 |
| Microcrystalline cellulose | 28.17 | 42.25 | 84.5 | 14.83 |
| Lactose monohydrate | 17 | 25.5 | 51 | 8.95 |
| Croscarmellose sodium | 5 | 7.5 | 15 | 2.63 |
| Povidone K-29/32 | 3.33 | 5 | 10 | 1.75 |
| Purified water | q.s | q.s | q.s | q.s |
| Crospovidone | 6 | 9 | 18 | 3.16 |
| Magnesium stearate | 2 | 3 | 6 | 1.05 |
| Tablet weight | 190 | 285 | 570 | — |
| Opadry White | 3.8 | 5.7 | 11.4 | 2 |

The tablets were manufactured using the procedure comprising the following steps: lamivudine, isomalt, microcrystalline cellulose, lactose monohydrate, croscarmellose sodium was done in a rapid mixer granulator and mixed for 5 to 20 minutes. Binder solution (povidone K-29/32 in purified water) is added to contents of rapid mixer granulator and mixed to get dough mass. The dough mass was dried, and dried granules passed through #18.

The blending of ingredients including above dried granules, crospovidone, and magnesium stearate were weighted, transferred into a blender, and mixed to form a homogeneous power mixture; the resultant mixture was compressed into tablets of appropriate weight and hardness to obtain a lamivudine tablet; and optionally, the tablets can be coated.

The results of dissolution studies of lamivudine tablets 300 mg are shown below

| Time (minutes) | Epivir 300 mg | Lamivudine polymorphic form I tablets 300 mg |
|---|---|---|
| 5 | 98 | 96 |
| 10 | 99 | 98 |
| 15 | 99 | 98 |
| 30 | 100 | 98 |
| 45 | 100 | 98 |

Example 6

Zidovudine 300 Mg and Lamivudine 150 Mg Tablets

| Component | Weight (mg)/Tablet | % (w/w) |
|---|---|---|
| Lamivudine (form I) | 150 | 13.64 |
| Zidovudine | 300 | 27.27 |
| Isomalt | 602 | 54.73 |
| Crospovidone | 40 | 3.64 |
| Calcium Stearate | 8 | 0.72 |
| Tablet weight | 1100 | — |
| Opadry White | 22 | 2 |

The tablets were manufactured using the procedure comprising the following steps: lamivudine, zidovudine, isomalt, crospovidone and calcium stearate were weighted, transferred into a blender, and mixed to form a homogeneous power mixture; the resultant mixture was compressed into tablets of appropriate weight and hardness to obtain a lamivudine and zidovudine tablet; and optionally, the tablets can be coated.

Example 7

Tenfovir Disoproxil Fumarate 300 Mg and Lamivudine 300 Mg Tablets

| Component | Weight (mg)/Tablet | % (w/w) |
|---|---|---|
| Lamivudine (form I) | 300 | 27.27 |
| Tenfovir disoproxil fumarate | 300 | 27.27 |
| Isomalt | 452 | 41.09 |
| Crospovidone | 40 | 3.64 |
| Calcium Stearate | 8 | 0.73 |
| Tablet weight | 1100 | — |
| Opadry White | 22 | 2 |

The tablets were manufactured using the procedure comprising the following steps: lamivudine, tenfovir disoproxil fumarate, isomalt, crospovidone and calcium stearate were weighted, transferred into a blender, and mixed to form a homogeneous power mixture; the resultant mixture was compressed into tablets of appropriate weight and hardness to obtain a lamivudine and tenfovir disoproxil fumarate tablet; and optionally, the tablets can be coated.

Example 8

Abacavir 600 Mg and Lamivudine 300 Mg Tablets

| Component | Weight (mg)/Tablet | % (w/w) |
|---|---|---|
| Lamivudine (form I) | 300 | 25 |
| Abacavir sulfate eq to abacavir | 702.8 | 58.57 |
| Low-substituted hydroxy propyl cellulose | 15 | 1.25 |
| Croscarmellose sodium | 15 | 1.25 |
| Isomalt | 24 | 2 |
| Microcrystalline cellulose | 83.2 | 6.93 |
| Povidone K-29/32 | 15 | 1.25 |
| Purified water | q.s | — |
| Low-substituted hydroxy propyl cellulose | 15 | 1.25 |
| Colloidal silicon dioxide | 15 | 1.25 |
| Magnesium stearate | 15 | 1.25 |
| Tablet weight | 1200 | — |
| Opadry White | 24 | 2 |

The tablets were manufactured using the procedure comprising the following steps: lamivudine, abacavir sulfate, and low-substituted hydroxy propyl cellulose, croscarmellose sodium, isomalt, microcrystalline cellulose was done in a rapid mixer granulator and mixed for 5 to 20 minutes. Binder solution (povidone K-29/32 in purified water) is added to contents of rapid mixer granulator and mixed to get dough mass. The dough mass was dried, and dried granules passed through #18.

The blending of ingredients including above dried granules, low-substituted hydroxy propyl cellulose, colloidal silicon dioxide and magnesium stearate were weighted, transferred into a blender, and mixed to form a homogeneous power mixture; the resultant mixture was compressed into tablets of appropriate weight and hardness to obtain a lamivudine and abacavir tablet; and optionally, the tablets can be coated.

Example 9

Lamivudine Tablets

| Component | Weight (mg)/Tablet | | | % (w/w) |
|---|---|---|---|---|
| Lamivudine (form II) | 100 | 150 | 300 | 33.3 |
| Isomalt | 183.3 | 275 | 550 | 61.1 |
| Crospovidone | 12 | 18 | 36 | 4 |
| Calcium Stearate | 4.7 | 7 | 14 | 1.6 |
| Tablet weight | 300 | 450 | 900 | — |
| Opadry White | 7.5 | 11.25 | 22.5 | 2.5 |

The tablets were manufactured using the procedure comprising the following steps: lamivudine, isomalt, crospovidone and calcium stearate were weighted, transferred into a blender, and mixed to form a homogeneous power mixture; the resultant mixture was compressed into tablets of appropriate weight and hardness to obtain a lamivudine tablet; and optionally, the tablets can be coated.

We claim:

1. An oral solid pharmaceutical composition comprising lamivudine or pharmaceutically acceptable salts thereof, isomalt, and optionally one or more additional excipients, wherein lamivudine is in a polymorphic form.

2. The composition as claimed in claim 1, wherein the ratio of lamivudine to isomalt is about 1:0.2 to about 1:4.

3. The composition as claimed in claim 1, wherein the additional excipients comprises lubricant, disintegrant, binder, glidant, or fillers.

4. The composition as claimed in claim 3, wherein the lubricant is selected from the group consisting of stearic acid, a salt of stearic acid, talc, sodium stearyl fumarate, glyceryl behenate, magnesium silicate, calcium stearate, magnesium trisilicate, hydrogenated castor oil and mixtures thereof; the disintegrant is selected from the group consisting of sodium starch glycolate, starch, croscarmellose sodium, crospovidone, carboxymethyl cellulose calcium, carboxymethylcellulose sodium, magnesium aluminium silicate and mixtures thereof; the binder is selected from the group consisting of hydroxypropyl cellulose, polyvinylpyrrolidone k-30, low-substituted hydroxypropyl cellulose, starch and mixtures thereof; the filler is selected from the group consisting of calcium carbonate, dibasic calcium phosphate, lactose, magnesium carbonate, magnesium oxide, lactose anhydrous, microcrystalline cellulose, mannitol and mixtures thereof.

5. An oral solid pharmaceutical composition comprising an antiviral compound containing an effective amount of lamivudine or pharmaceutically acceptable salts thereof, and isomalt, wherein the ratio of lamivudine to isomalt is about 1:0.2 to about 1:4.

6. The composition as claimed in claim 5, wherein the antiviral compound consists of an effective amount of lamivudine or a pharmaceutically acceptable salt thereof and an effective amount of a second antiviral compound selected from the group consisting of zidovudine, abacavir, tenofovir disoproxil fumarate, or a mixture thereof.

7. The composition as claimed in claim 5, wherein the oral solid pharmaceutical composition in the form of a tablet, a caplet, a pellet, a capsule, a granule, a pill, a powder or a sachet.

8. The composition as claimed in claim 5, wherein the antiviral compound consists of an effective amount of lamivudine and an effective amount of zidovudine.

9. The composition as claimed in claim 5, wherein the antiviral compound consists of an effective amount of lamivudine and an effective amount of abacavir.

10. The composition as claimed in claim 5, wherein the antiviral compound consists of an effective amount of lamivudine and an effective amount of tenofovir disoproxil fumarate.

11. The composition as claimed in claim 5, wherein the lamivudine is in polymorphic form I.

12. The composition as claimed in claim 1, wherein lamivudine is present in form I after being stored for about two months under the condition of 75% relative humidity at 40° C., or 75% relative humidity at 60° C.

13. The composition as claimed in claim 1, further comprising crospovidone and calcium stearate, wherein the lamivudine is present in the amount of about 25% to 80%, the isomalt is in the amount of about 15% to 80%, the crospovidone is in the amount of about 1% to 10%, and calcium stearate is in the amount of about 0.125% to 5% of the total weight of the composition.

14. The composition as claimed in claim 8, further comprising crospovidone, calcium stearate wherein the lamivudine is present in the amount of 10% to 25%, zidovudine is in the amount of about 15% to 40%, the isomalt is in the amount of about 15% to 70%, the crospovidone is in the amount of about 1% to 10%, and calcium stearate is in the amount of about 0.125% to 2.5% of the total weight of the composition.

15. The composition as claimed in claim 9, further comprising low-substituted hydroxyl propyl cellulose, croscarmellose sodium, microcrystalline cellulose, povidone K-29/32, colloidal silicon dioxide and magnesium stearate, wherein the lamivudine is present in the amount of about 15% to 25%, abacavir sulfate is in the amount of about 30% to 75%, the isomalt is in the amount of about 1% to 50%, the low-substituted hydroxyl propyl cellulose is in the amount of about 3% to 25%, the povidone is in the amount of about 1% to 7%, the colloidal silicon dioxide is in the amount of about 0.125% to 2.5%, the magnesium stearate is in the amount of 0.125% to 2.5% of the total weight of the composition.

16. The composition as claimed in claim 10, further comprising crospovidone, and calcium stearate, wherein the lamivudine is present in the amount of 10% to 60%, tenofovir disoproxil fumarate is in the amount of about 15% to 50%, the isomalt is in the amount of about 15% to 70%, the crospovidone is in the amount of about 1% to 10%, and calcium stearate is in the amount of about 0.125% to 2.5% of the total weight of the composition.

* * * * *